United States Patent
Baldwin et al.

(10) Patent No.: US 8,766,652 B2
(45) Date of Patent: Jul. 1, 2014

(54) METHOD AND APPARATUS FOR MEASURING THE GRAIN ANGLE OF A ROUND WOOD OBJECT

(75) Inventors: Ryan D. Baldwin, Pullman, WA (US); Harry E. Moore, Moscow, ID (US); James D. Logan, Pullman, WA (US)

(73) Assignee: Metriguard, Inc, Pullman, WA (US)

( * ) Notice: Subject to any disclaimer, the term of this patent is extended or adjusted under 35 U.S.C. 154(b) by 458 days.

(21) Appl. No.: 13/315,206

(22) Filed: Dec. 8, 2011

(65) Prior Publication Data

US 2012/0146617 A1 Jun. 14, 2012

Related U.S. Application Data

(60) Provisional application No. 61/459,503, filed on Dec. 13, 2010.

(51) Int. Cl.
*G01R 27/26* (2006.01)
*G01N 33/46* (2006.01)
*G01N 27/22* (2006.01)

(52) U.S. Cl.
CPC .............. *G01N 27/221* (2013.01); *G01N 33/46* (2013.01)
USPC .......................................................... 324/663

(58) Field of Classification Search
CPC ...... G01N 27/221; G01N 27/22; G01N 33/46
USPC .................................................. 324/663, 71.1
See application file for complete search history.

(56) References Cited

U.S. PATENT DOCUMENTS

| 4,926,350 A | * | 5/1990 | Bechtel et al. | 702/36 |
| 5,394,097 A | * | 2/1995 | Bechtel et al. | 324/687 |
| 6,305,224 B1 | * | 10/2001 | Stanish et al. | 73/597 |

* cited by examiner

*Primary Examiner* — Amy He (57) ABSTRACT

This invention provides a method and apparatus for determining the grain angle of a wood object which has a circular cross section of constant or varying radius along the object's length. This apparatus may be hand-held or fixed mounted as testing circumstances dictate. The resulting grain angle may be displayed in real time, as perceived by the user, or transmitted to a processing unit for data collection or interpretation.

11 Claims, 7 Drawing Sheets

METHOD AND APPARATUS FOR MEASURING THE GRAIN ANGLE OF A ROUND WOOD OBJECT

CROSS-REFERENCE TO RELATED APPLICATIONS

1. Method and Apparatus for Measuring the Grain Angle of a Round Wood Object; Provisional application filed Dec. 13, 2010, Application No. 61/459,403

REFERENCES

1. U.S. Pat. No. 4,972,154; Nov. 20, 1990; Apparatus and Method for Measuring Wood Grain Angle; Bechtel et al.; Assignee: Metriguard Inc.
2. U.S. Pat. No. 5,654,643: Aug. 5, 1997; Dielectric Sensor Apparatus; Bechtel et al.; Assignee: Metriguard Inc.

TECHNICAL FIELD

This invention relates to the field of non-destructive measurement of the properties of wood object, namely the grain angle of a round wood object to determine its structural properties in which excessive stresses can lead to failure.

IMPORTANCE OF THE INVENTION AND PRIOR ART

The angle of the longitudinal axis of the cells in an object made of wood, correlate directly with the stiffness and strength of the object—that is, if this axis is perpendicular in both orthogonal planes to the direction of applied force, the stiffness and strength of the object will be at a maximum. This is an important observation that lends itself to analysis of objects such as baseball bats, golf clubs, guitar necks and like objects subject to breakage under loading. In addition to safety concerns, the expense of such breakage is an obvious concern.

To date, there is no convenient and repeatable method of measuring this grain angle in curved surfaces. In some species of wood, such as maple and birch, due to their extremely fine grain, direct observation of this grain angle is difficult, time consuming, and subjective. Whereas the technology exists to measure the grain angle of flat surfaces (see U.S. Pat. No. 4,972,154) curved surfaces, such as the blanks used in the fabrication baseball bats, cannot be measured by any apparatus. Currently, the accepted grain angle measurement technique is the placing of an ink blot on the sample's surface and observing the pattern of ink spread along the grain. These tests are time consuming and the results are subject to the interpretation of the user and consequently vary widely.

This invention is in direct response to an increase in the occurrence of broken baseball bats in Major League Baseball, and the hazards associated with these breaks. The frequency of bat failures has increased with a shift from using White Ash as the bat material to Sugar Maple, commonly known as Hard Maple. Although Sugar Maple is harder and stiffer than White Ash, bats made from maple tend to fail due to excessive slope-of-grain. Slope-of-grain is the angle between the long axis of a wood object and the direction of the wood fibers, and is a major factor in the strength of a wood object. As the slope-of-grain, or grain angle, increases, strength decreases significantly. In the case of a baseball bat, slope-of-grain failures typically display an oval shaped fracture plane (following the grain angle) somewhere in or near the handle section of the bat, and involve large pieces of the head of the bat entering the field of play and spectator areas in uncontrolled flight. Major League Baseball now specifies slope-of-grain of three degrees or less. However, maple is a diffuse-porous wood with exceptionally fine grain size. This makes visually finding the preferred grain orientation very difficult, and has led to the use of the ink dot method of grain angle detection.

SUMMARY OF PRESENT INVENTION

In order to determine the grain angle of a wood object with a curved surface, the present invention adds a series of guides to track the curved surface and keep the invention's dielectric sensor (see U.S. Pat. No. 4,972,154) both centered and tangent to the surface of the wood object. While these guides provide a stable and repeatable measurement, the resulting measured values will be skewed by the radius of the object at the point of measurement. The measurement error, zero at a zero grain angle and increasing with increasing grain angle, is caused by the fall off of the dielectric sensor's electric field in the sample as the sample's curved surface becomes increasingly further away from the flat dielectric sensor plate. To correct this skew, the preferred embodiment of the present invention incorporates continuous angle correction by detecting the curved surface radius. The means of detection can be a sensor coupled to self-adjusting guides. The sensor may be a rotary encoder, a potentiometer, a variable inductor, a magneto-restrictive sensor or employ any other suitable sensing method. The correction may be linear with the application of a correction scalar and offset, by a higher order correction algorithm, and/or through a series of self-contained look up tables to provide appropriate adjustment as the radius of the sample varies.

As an alternative preferred embodiment, the dielectric sensor may consist of a flexible printed circuit board, contoured to follow the surface of wood object of fixed radius. This dielectric sensor plate may be configured to plug in and be interchangeable with sensor plates of different curvatures for measuring a range of wood object shapes.

A further preferred embodiment may, in addition to the guides above, employ a flat dielectric sensor but with dielectric plates with distorted geometry to concentrate the electric field in the direction perpendicular to the axis of the object under test. The dielectric plates will be elongated and or widened on this axis to increase the concentration of the electric field where the curvature of the object under test increases the distance to the flat dielectric plate.

BRIEF DESCRIPTION OF THE DRAWINGS

A preferred embodiment of the invention is illustrated in the accompanying drawings, in which.

DETAILED DESCRIPTION OF THE PREFERRED EMBODIMENT

Figure 1:
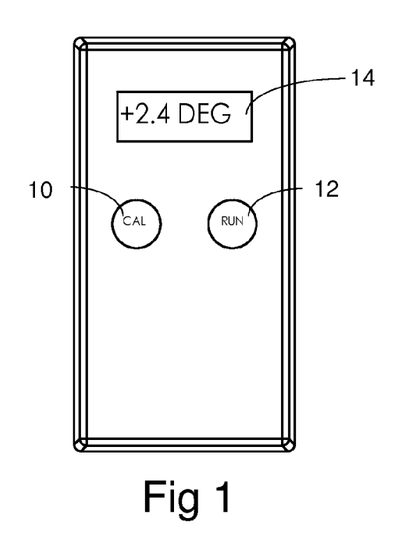
FIG. 1 illustrates a schematic top view of the grain angle meter.

FIG. 1 is a top view of a hand-held version of the grain angle meter. The CAL or calibrate button 10 is pressed to establish a zero signal reference for further measurements and is activated when the meter is removed a distance from the object to be tested. The RUN button 12 is held down for continuous readings when the meter is placed over a wooden object. The indicator screen 14 may employ liquid crystal (LCD), light emitting diode (LED), or any other display method or rely on an external display and/or data collection system to interface to the operator.

Figure 2:
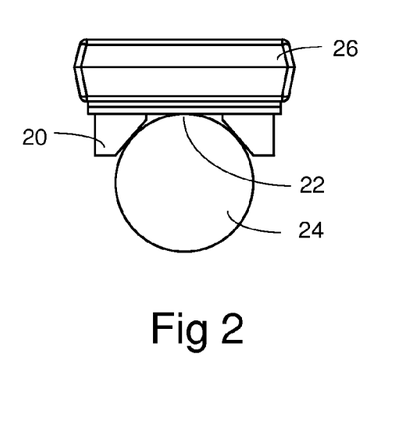
FIG. 2 illustrates a schematic end view of the grain angle meter with fixed guides and cylindrical wooden object.

FIG. 2 is an end view showing fixed guides 20, which center the wooden object 24 over the meter 26. Said fixed guides center the wood sample under test while allowing the meter's dielectric sensor 22 to be tangent to the sample's surface. Said fixed guides will function with wood samples of a predetermined radius such as found in baseball bat blanks and other partially processed wood objects. Grain angle meters built for this purpose will have a predetermined compensation algorithm to adjust for the radius of the wood sample under test.

Figure 3:
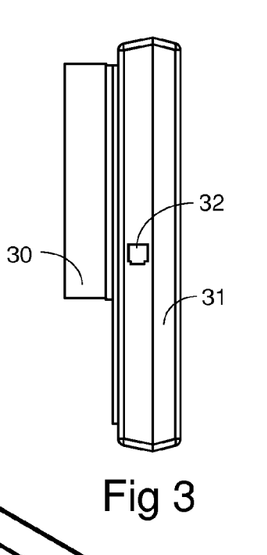
FIG. 3 illustrates a schematic side view of the grain angle meter with fixed guides.

FIG. 3 is a side view showing the extent of the fixed guides 30 in relation to the meter case 31. Also displayed is a data port 32 which may be used to send data to a remote display and processing device, load new firmware into the meter, or simply permit powering the device with an external power source.

Figure 4:
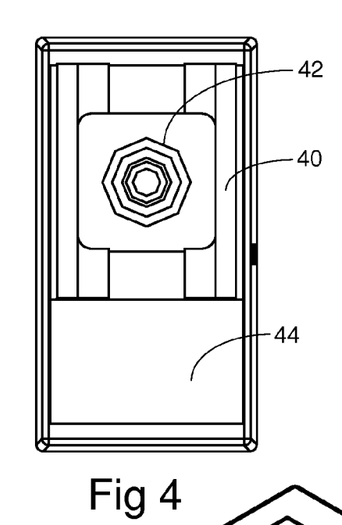
FIG. 4 illustrates a schematic bottom view of the grain angle meter with fixed guides and dielectric plate.

FIG. 4 shows a bottom view and the position of the dielectric plate 42 in relation to the fixed guides 40. Note that the conductors on the dielectric plate are not normally visible and are covered with a thin layer of dielectric material such as polyethylene. Also shown is the cover for the meter's batteries 44.

Figure 5:
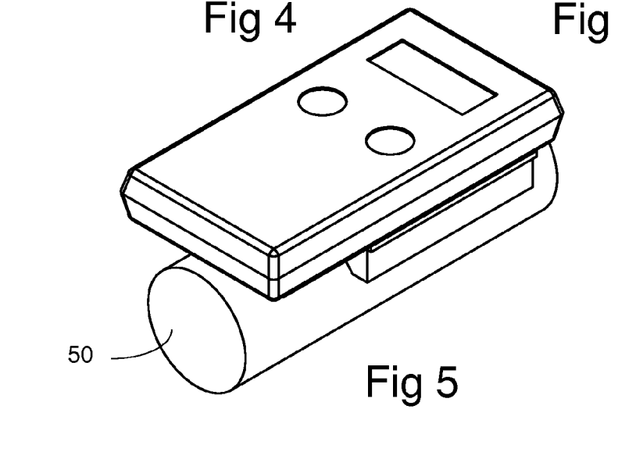
FIG. 5 illustrates a perspective view of the grain angle meter in relation to a cylindrical wooden object.

FIG. 5 is a perspective view of the meter in use with a round wooden object 50, such as a baseball bat blank, under test.

Figure 6:
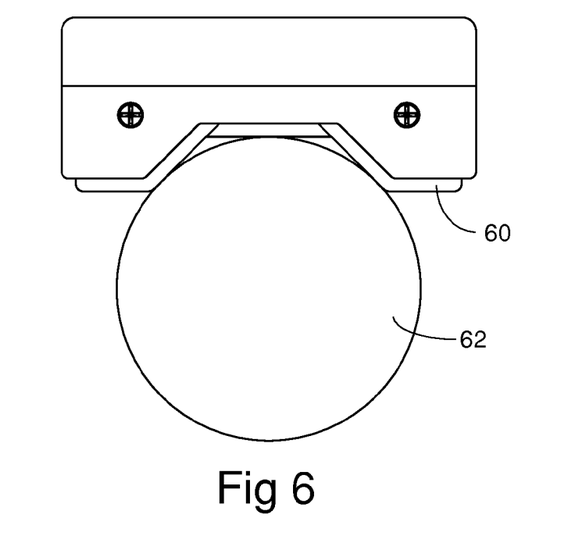
FIG. 6 illustrates a schematic end view of self-adjusting guide in relation to large radius cylindrical object.

FIG. 6 shows a self-adjusting V-shaped guide 60 hat automatically centers a variable radius wood object under the meter's sensor plate. A large radius wood object 62 is shown under test.

Figure 7:
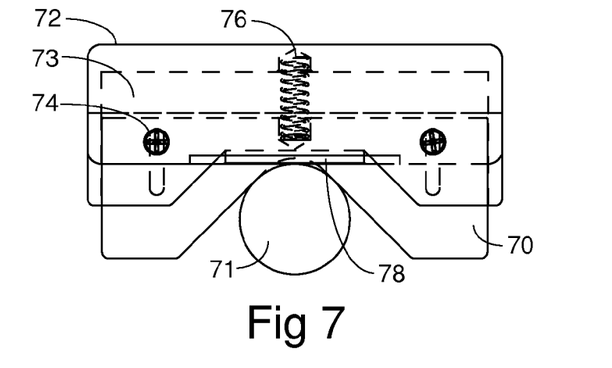
FIG. 7 illustrates a schematic end view of self-adjusting guide in relation to small radius cylindrical object.

FIG. 7 shows this same guide configuration but tracking a small diameter wood object 71. The V-blocks 70 adjust for different radii by sliding vertically with respect to the meter body 73, along guide rods 74, which are fixed to a plate 72. Compression springs 76 keep the guide pressed against the object under test 71. The V-blocks are fully extended when not in use, and the operator must place the centers of the V-blocks 70 over the test subject 71, and lightly push the body of the meter down until the test subject is in contact with the sensor plate 78.

Figure 8:
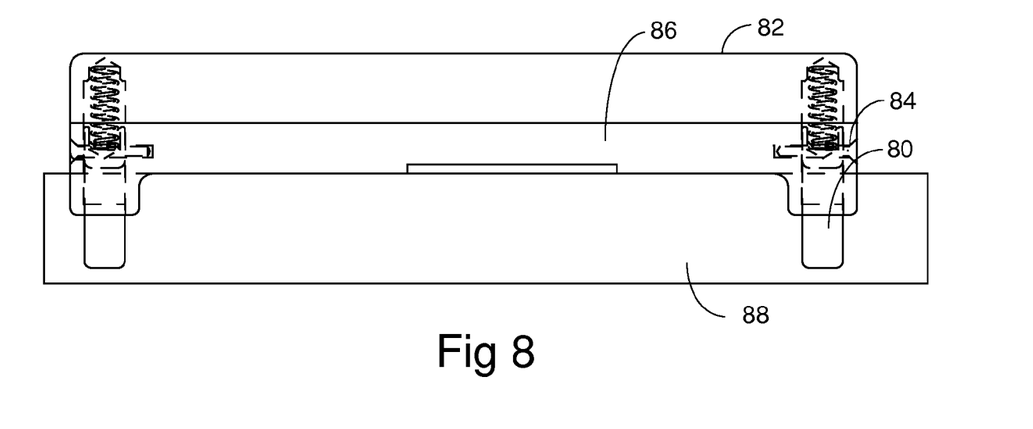
FIG. 8 illustrates a schematic side view of grain angle meter and self-adjusting guide.

FIG. 8 shows the side view of the meter with said guide 80 attached to the front of the meter by way of guide rods 84 fastened to a mounting plate 82. Note that a second guide is similarly placed at the rear of the meter, with the centers of the V-blocks parallel to the centerline of the long axis of the meter body 86. This forces the object under test 88 to be centered and parallel with respect to the long axis of the meter body.

Figure 9:
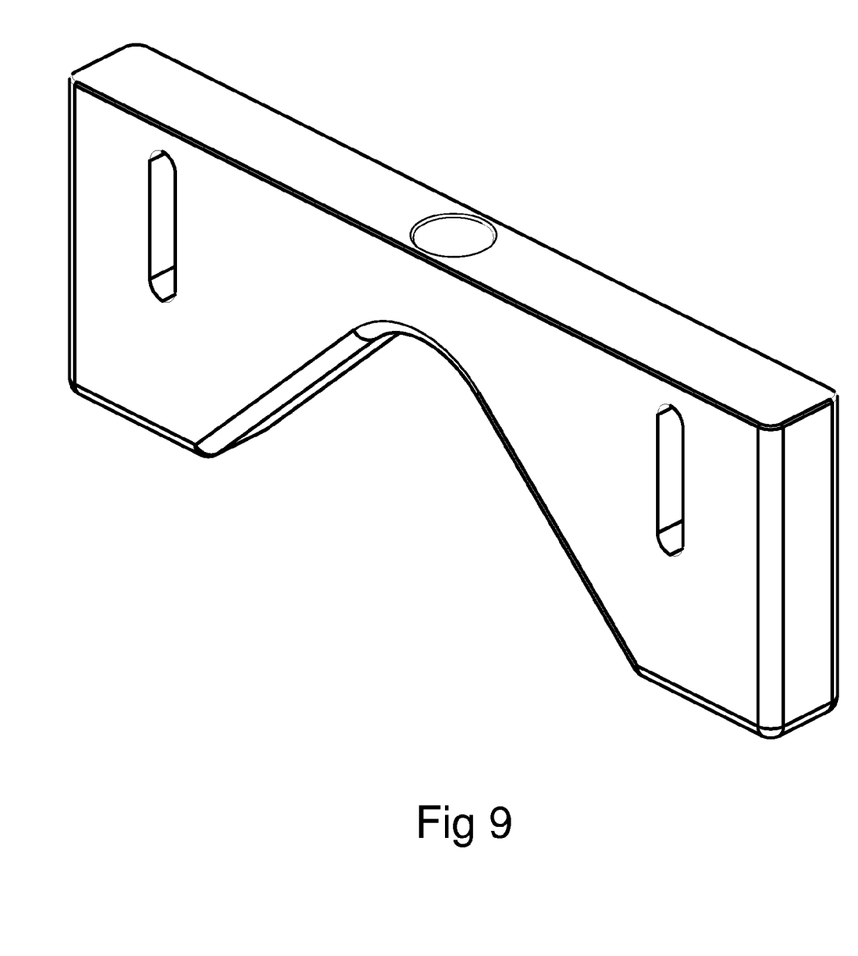
FIG. 9 is a perspective view of the V-shaped guide.

FIG. 9 is a perspective three-dimensional view of the V-shaped guide showing the guide's internal channels for guide rods and springs.

Figure 10:
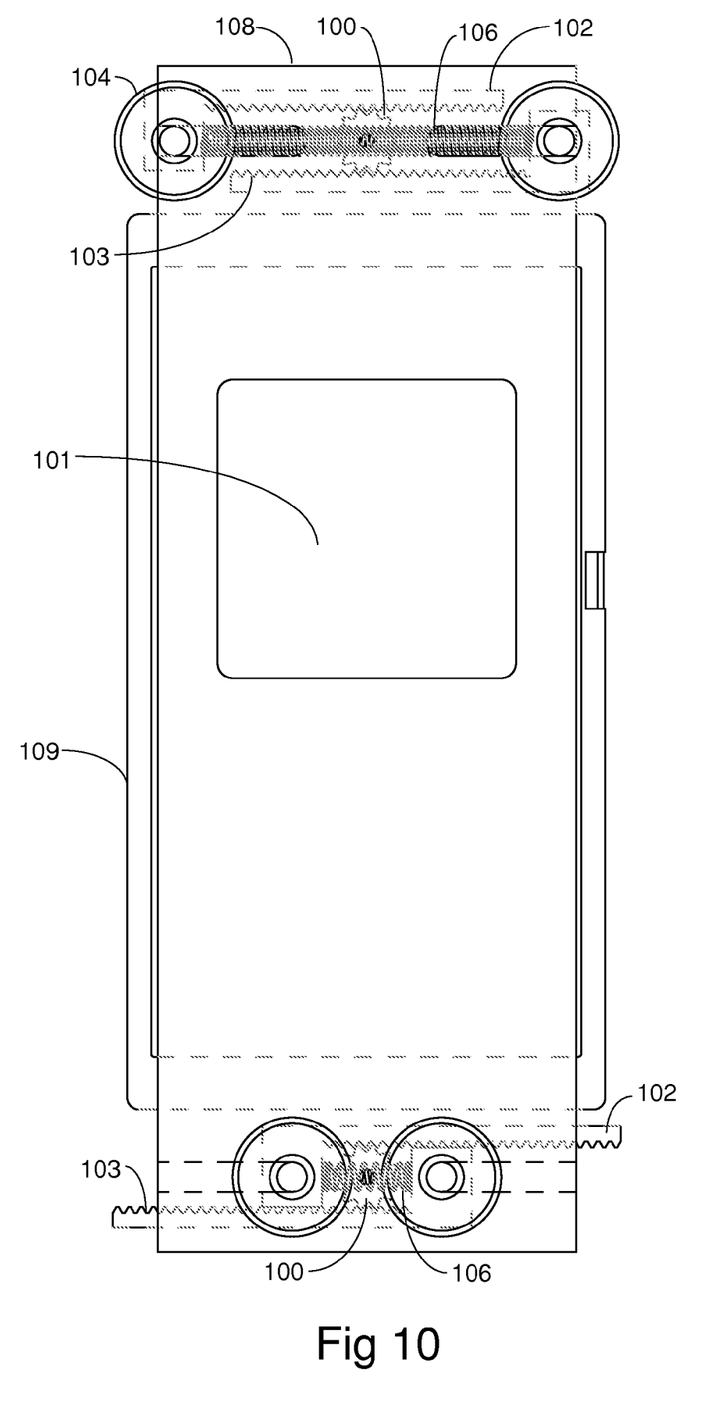
FIG. 10 illustrates a schematic bottom view of the grain angle meter with self-adjusting roller guides.

FIG. 10 shows the bottom view of a meter with roller guides to center a variable radius object over the meter's dielectric sensor 101. In this configuration, two wheels 104 are rotatably attached at opposite ends of racks 102 and 103 that are slidably attached to the mounting plate 108. Racks 102 and 103 are mounted diametrically opposed, and teeth meshed with rotatably attached pinion 100. As one wheel is urged to move with respect to the meter 110 by the object under test, the pinion forces the other guide wheel to move the same rate and distance in the opposite direction. Extension springs 106 keep the wheels in contact with the wood object under test.

Figure 11:
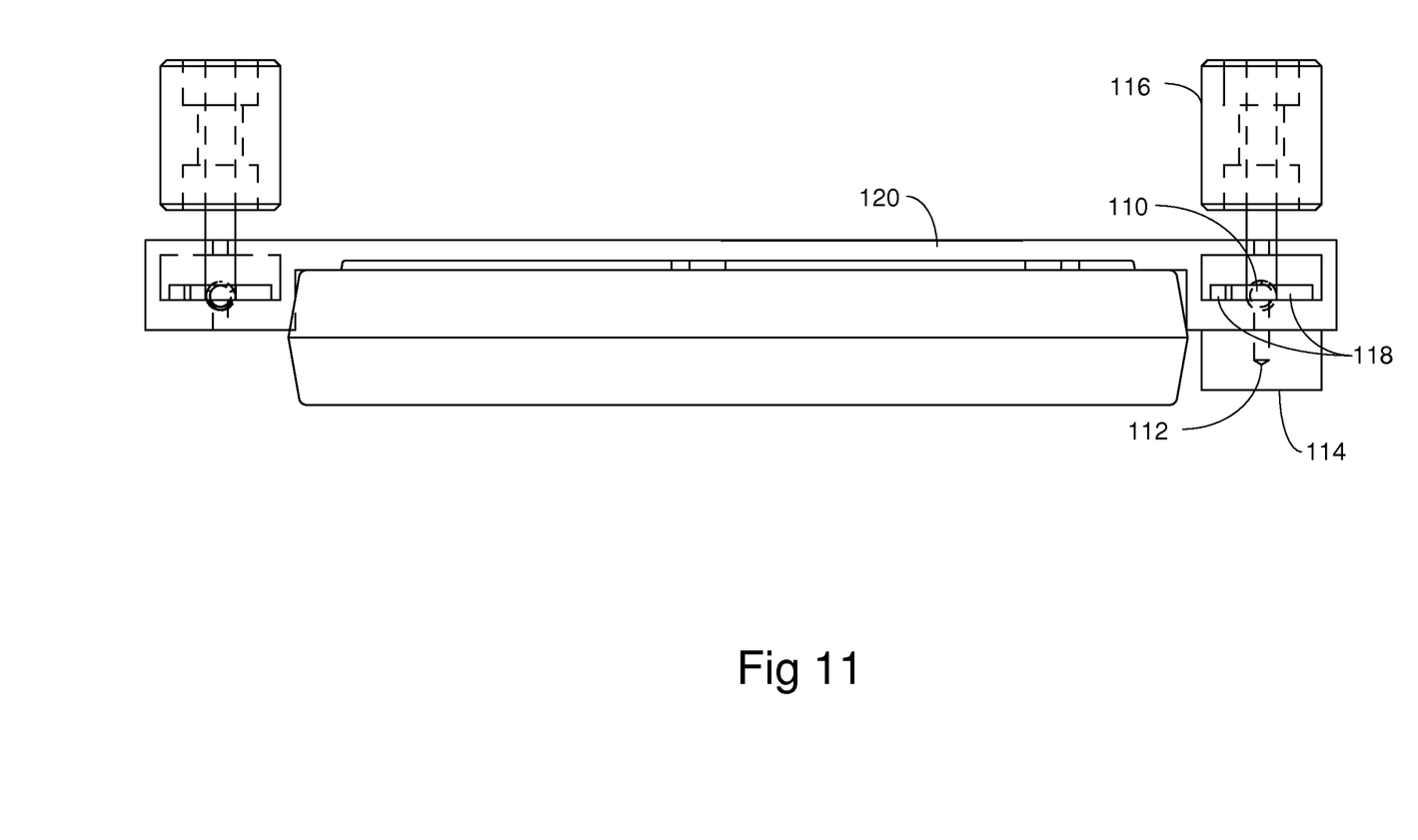
FIG. 11 illustrates a schematic side view of the grain angle meter with self-adjusting roller guides.

FIG. 11 shows a side view of this same sensor configuration but with the addition of a guide extension sensor 114 which provides feedback to the meter's electronics for continuous compensation of the grain angle reading with variable radius wooden objects such as completed baseball bats. The sensor 114, may be a rotary encoder, or a potentiometer, and driven by a shaft 112, which is fixed to the pinion 110, which is rotably attached to the mounting plate 120.

Figure 12:
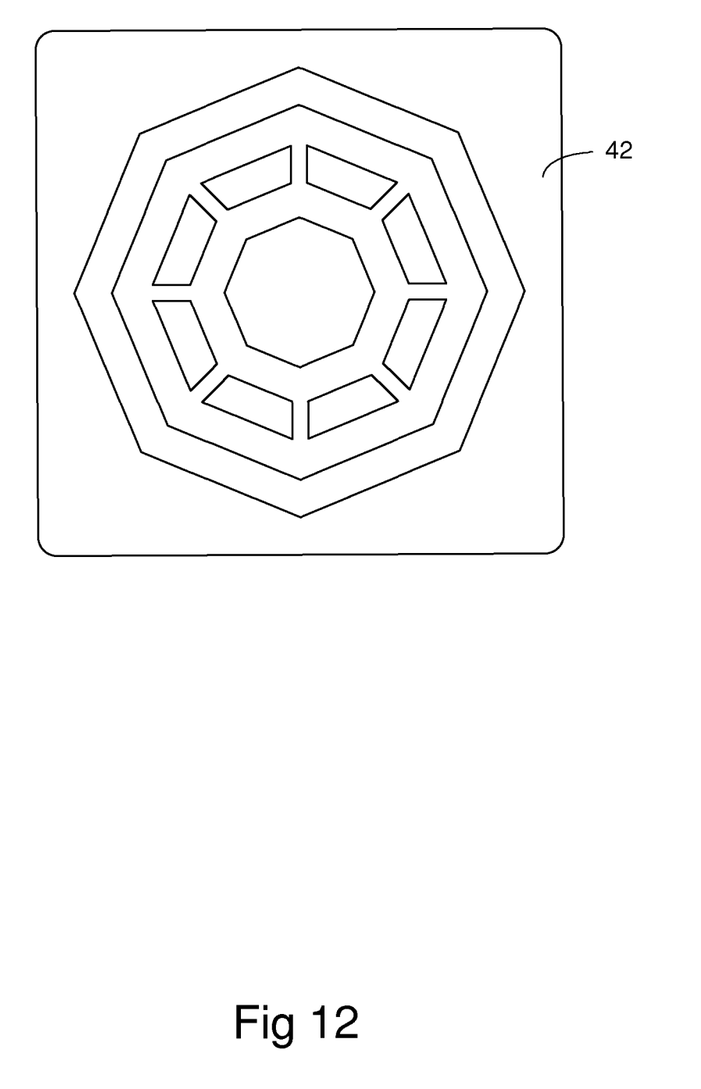
FIG. 12 illustrates a schematic top view of the dielectric plate for grain angle detection on flat surfaces.

FIG. 12 shows a top view of the dielectric plate used in U.S. Pat. No. 5,654,643 for grain angle detection on flat wood surfaces.

OTHER EMBODIMENTS OF THE INVENTION

If it is desired to mount the grain angle meter in a fixed position, it may be mounted on a stand and wood samples moved through its guides. This may be a more desirable configuration in areas such as baseball dugouts where bats can be checked before use for excessive grain angle.

Figure 13:
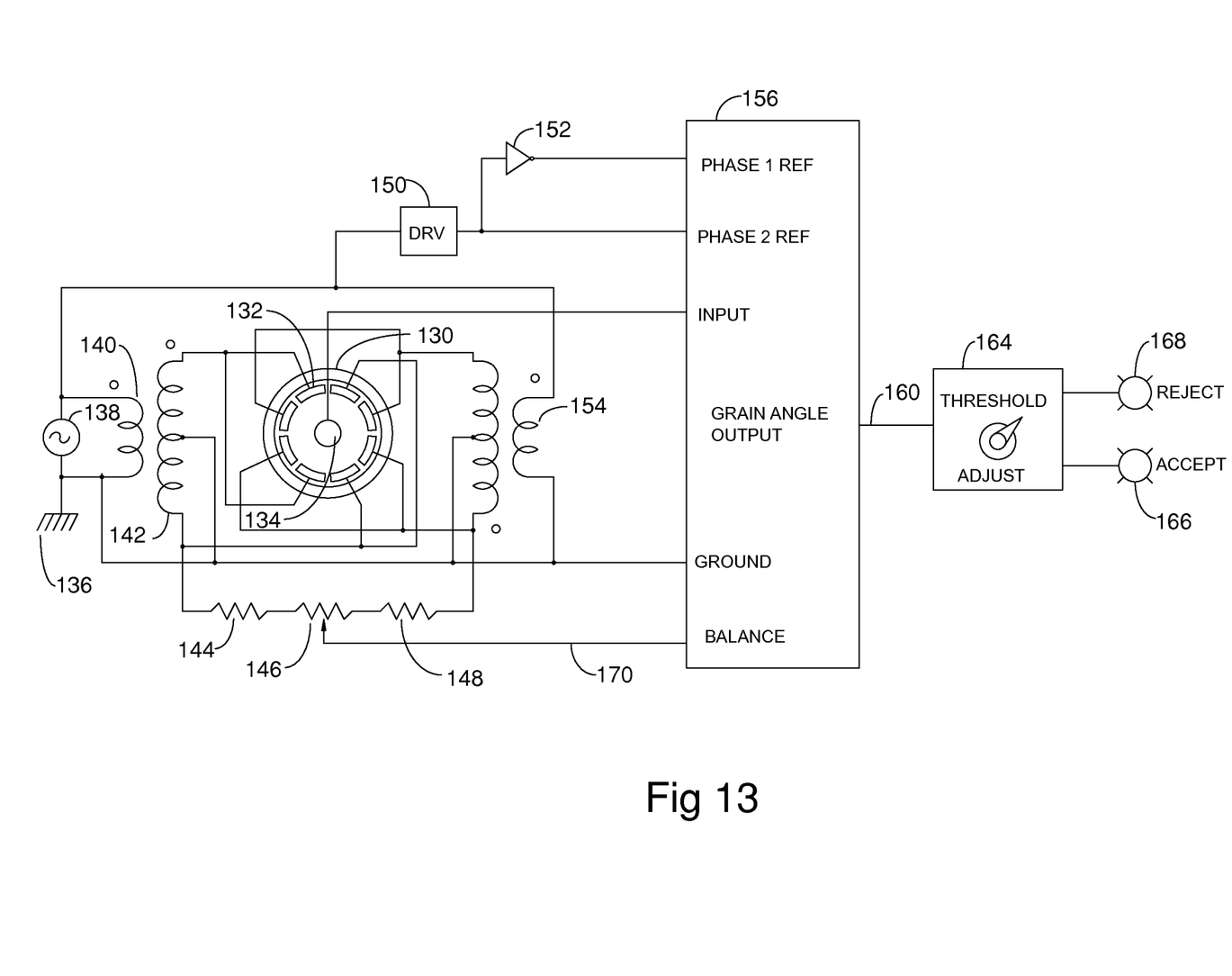
FIG. 13 depicts a schematic block diagram illustrating a grain angle measuring device that indicates only if the measured grain angle is above or below a predetermined threshold.

In an additional preferred embodiment shown in FIG. 13, a grain angle detector is implemented with only "ACCEPT" 166 and "REJECT" 168 indicator lights as output to the operator.

An oscillator of predetermined electrical frequency and voltage output 138 is connected to the primary coils of two transformers 140 and 154 with coil polarities as shown. In an alternative preferred embodiment, a single transformer is used with a primary winding and two identical center-tapped secondary windings 142. The outputs of the two secondary transformer windings are connected to sensor plate 130, which sensor plate includes sector electrodes 132 arranged in a circle. The alternating voltages and phases on sequential sector plates produce a rotating electric field vector in the space adjacent sensor electrode 134, the electric charge magnitude and phase angle induced on sensor plate 134 is influenced by the electric permittivity vector in material adjacent the sensor plate 130. Said sensor electrode 134 is connected to grain angle determining circuitry 156 along with phase 1 and phase 2 references from driver (DRV) 150 and inverter 152, and a balance signal 170 derived the opposite-phase signals from transformer secondary windings 142, reduced by voltage divider composed of resistors 144, 148, and potentiometer 146. Balance input 170 is used to compensate for minor electric imbalances in the circuit and is not operator adjustable. Circuit ground 136 is internal only and is not normally connected to earth ground, but rather provides a common electrical potential for internal references and shielding.

Grain angle output 160 from grain angle computation 156 is connected to adjustable threshold adjustment 162 whereby grain angles detected below a predetermined threshold will show an "ACCEPT" indication and those above said predetermined threshold will indicate a "REJECT" indication. Adjustment 164 may be changed during a calibration process then locked in place.

In operation a wood specimen is placed adjacent sensor plate 130 in a preferred directional orientation with respect to the long axis of the wood specimen, the circuitry is activated and indicators 166 and 168 indicate ACCEPT or REJECT condition based on the wood grain angle in the specimen.

APPARATUS

In compliance with the statute, the invention has been described in language more or less specific as to structural features. It is to be understood, however, that the invention is not limited to the specified features shown, because the means and construction herein disclosed comprise a preferred form of putting the invention into effect. The invention is, therefore, claimed in any of its forms or modifications within the proper scope of the appended claims appropriately interpreted in accordance with the doctrine of equivalents.

The invention claimed is:

1. An improved apparatus for measuring grain angle in a round wood object, said round wood object having an axis and a substantially circular cross-section with or without varying radius, comprising an electronic grain angle measurement means with a dielectric wood grain angle sensor means having a center point, a positioning means for aligning said round wood object such that a point on a surface of said round wood object is in close proximity to said center point of said dielectric wood grain angle sensor and said axis of said round wood object is at a known relationship to an axis of said dielectric wood grain angle sensor, a compensation means for reducing the effects of electric field distortion by said round wood object, and an indicator means, whereby the grain angle of a round wood object is determined.

2. The apparatus of claim 1 in which said indicator means includes a readout whereby grain angle in degrees is displayed.

3. The apparatus of claim 1 in which said indicator means includes a readout whereby grain angle expressed as a ratio of rise over run is displayed.

4. The apparatus of claim 1, including one or more threshold means, each with an output means, for grading of said round wood object whereby a preferred maximum limit of grain angle is established for each said threshold means such that corresponding said output means is activated when grain angle exceeds said preferred maximum limit of grain angle.

5. The apparatus of claim 1, including a manual zero means and a control means whereby said indicator is adjusted to indicate zero while said dielectric wood grain angle sensor is removed from vicinity of said round wood object while said control is activated.

6. The apparatus of claim 1, including an auto-zero means in which said indicator means is adjusted to indicate zero whenever said dielectric wood grain angle sensor is not significantly influenced by the presence of said round wood object.

7. The apparatus of claim 1 in which said positioning means moves in response to said varying radius of said round wood object whereby said point on surface of said round wood object is maintained in a position near said center point of said dielectric wood grain angle sensor.

8. The apparatus of claim 7 in which said position means includes one or more roller pairs, each with rollers of length sufficient to engage a surface of said round wood object and each said roller pair spring loaded to urge each said roller toward a central position and connected by a linkage means whereby said rollers of said roller pair are equidistance from said axis of said round wood object.

9. The apparatus of claim 1 in which said positioning means is comprised of one or more V-block means shaped to engage a surface of said round wood object.

10. The apparatus of claim 9 in which one or more of said V-block means are mounted on a slide assembly means to allow relative motion between said axis of said round wood object and said center point of said dielectric wood grain angle sensor as said radius of said round wood object varies.

11. The apparatus of claim 1 including a sensor means which detects said radius of said round wood object and adjusts said compensation means as said radius varies.

* * * * *